US00PP08692P

United States Patent [19]

Warriner, deceased

[11] Patent Number: Plant 8,692

[45] Date of Patent: Apr. 19, 1994

[54] FLORIBUNDA ROSE PLANT NAMED 'JACOUT'

[75] Inventor: William A. Warriner, deceased, late of Tustin, Calif., by Alene Beatrice Warriner, executor

[73] Assignee: Bear Creek Gardens, Inc., Medford, Oreg.

[21] Appl. No.: 23,881

[22] Filed: Feb. 17, 1993

[51] Int. Cl.[5] ..... A01H 5/00

[52] U.S. Cl. ..... Plt./28

[58] Field of Search ..... Plt. 22, 27, 28

*Primary Examiner*—Howard J. Locker

*Attorney, Agent, or Firm*—Klarquist, Sparkman, Campbell, Leigh and Whinston

[57] ABSTRACT

A floribunda rose having a strong flower fragrance; ease of production by softwood and hardwood cuttings and by budding; vigorous, upright and well-branched growth habit; and distinctive, deep pink flower color.

1 Drawing Sheet

The present invention relates to a new and distinct variety of rose plant of the floribunda class which was originated by the inventor by crossing the variety JACum, U.S. Plant Pat. No. 5,002, with the variety JACdew, U.S. Plant Pat. No. 5,122.

The primary objective of this breeding was to produce a new rose variety having the fragrance and growth habit of the female parent combined with the disease resistance and vigor of the male parent. The objective was substantially achieved along with other desirable improvements as evidenced by the following unique combination of characteristics which are outstanding in the new variety and which distinguish it from its parents, as well as from all other varieties:

1. Upright, vigorous, well-branched growth habit;
2. Strong, sweet fragrance;
3. Distinctive, deep pink flower color; and
4. Ease of propagation by hardwood and softwood cuttings, as well as by budding.

Asexual reproduction of this new variety by budding and by softwood and hardwood cuttings, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with the Royal Horticultural Society (London) Colour Chart, except where ordinary dictionary significance of color is indicated.

Parentage:

*Seed parent.*—JACum, U.S. Plant Pat. No. 5,002.

*Pollen parent.*—JACdew, U.S. Plant Pat. No. 5,122.

Classification:

*Botanical.*—*Rosa hybrida.*

*Commercial.*—Floribunda.

FLOWER

Observations made from specimens grown in a garden environment in Somis, Calif., from April through November, 1992.

Blooming habit: Recurrent.

Bud:

*Size.*—1 inch when the petals start to unfurl.

*Form.*—Short, pointed ovoid.

*Color.*—When sepals first divide, bud color is Red Group 50A. When half blown, the upper sides of the petals are Red Group, 50A; and the lower sides of the petals are Red Group 50A except outside guard petals that have a light, broad streak of Red Group 50B to 50C.

*Sepals.*—Color: Green Group 138C. Surface texture: Covered in fine hairs. There are three normally appendaged sepals. There are two unappendaged sepals with hairy edges.

*Receptacle.*—Color: Green Group 138B. Shape: Funnel. Size: Small ($\frac{1}{4}\times\frac{1}{4}$ inch). Surface: Smooth.

*Peduncle.*—Length: Medium ($2\frac{1}{2}$ inches). Surface: Glandular. Color: Light green. Strength: Stiff, erect.

Bloom:

*Size.*—Medium. Average open size is $3\frac{1}{2}$ inches.

*Borne.*—Singly and several together, in clusters. If in clusters: Rounded.

*Stems.*—Short (8–10 inches).

*Form.*—When first open: High centered. Permanence: Flattens, outer petals curl back.

*Petalage.*—Number of petals under normal conditions: 20–25.

*Color.*—The upper and reverse sides of the petals are Red Group 50A. The base of each petal has a yellow half mnoon ($\frac{3}{8}\times\frac{3}{8}$ inch at the point of attachment. The major color on the upper side is Red Group 50A.

*Variegations.*—Occasional white streak on guard petals.

*Discoloration.*—The general tonality at the end of the first day: No change. At the end of the third day, No change. Under intense sunlight, flowers will fade to a light lavender by the end of day 5 or 6.

*Fragrance.*—Strong.

Petals:

*Texture.*—Thick.

*Shape.*—Round.

*Form.*—Tips slightly recurved.

*Arrangement.*—Imbricated, with few petaloids in the center.

*Persistence.*—Drop off cleanly.

*Lastingness.*—On the plant: Fair (5 or 6 days). As a cut flower: Fair (6 days).

Reproductive parts:

*Anthers.*—Size: Medium. Quantity: Many. Color: Yellow. Arrangement: Regular around styles.

*Filaments.*—Color: Yellow.

*Pollen.*—Color: Gold yellow.

*Styles.*—Color: White.

*Stigmas.*—Color: Red.

Form: Bush.

Growth: Vigorous, upright, branching.

Foliage:

*Number of leaflets on normal mid-stem leaves.*—5 or 7.

*Size.*—Medium (6×4 inches).

*Quantity.*—Abundant.

*Color.*—New foliage: Reddish. Old Foliage: Dark green.

Leaflets:

*Shape.*—Pointed oval.

*Texture.*—Upper side: Leathery.

*Edge.*—Serrated.

*Serration.*—Single, small.

*Petiole rachis.*—Color: green.

*Petiole underside.*—Rough, with prickles.

*Stipules.*—Medium, smooth, bearded.

*Disease resistance.*—Susceptible to mildew but resistant to rust under normal growing conditions at Somis, Calif.

Wood:

*New wood.*—Color: Light green. Bark: Smooth.

*Old wood.*—Color: Green. Bark: Smooth.

Prickles:

*Quantity.*—On main canes from base: Ordinary. On laterals from main canes: Ordinary.

*Form.*—Medium, straight.

*Color when young.*—Red.

Small prickles:

*Quantity.*—On main stalks: None. On laterals: None.

It is claimed:

1. A new and distinct variety of rose plant of the floribunda class, substantially as herein shown and described, characterized particularly as to novelty by the unique combination of its strong flower fragrance; ease of production by softwood and hardwood cuttings and by budding; vigorous, upright and well-branched growth habit; and distinctive, deep pink flower color.

* * * * *

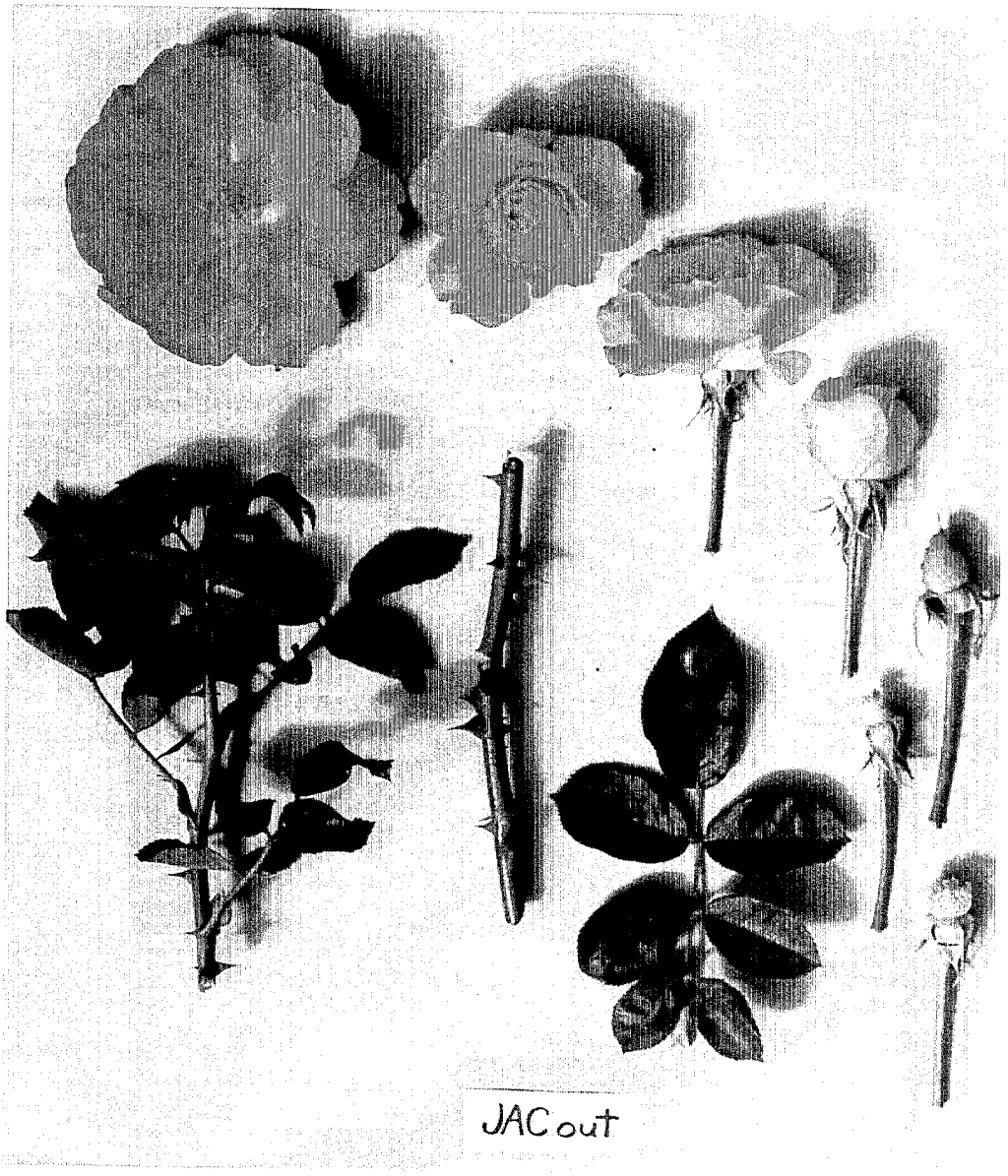
JAC out